United States Patent
Yamaguchi et al.

(10) Patent No.: US 8,519,078 B2
(45) Date of Patent: Aug. 27, 2013

(54) POLYETHER-MODIFIED POLYSILOXANE CONTAINING A PERFLUOROPOLYETHER GROUP AND ITS PRODUCTION METHOD

(75) Inventors: Hiromasa Yamaguchi, Annaka (JP); Yasunori Sakano, Annaka (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 164 days.

(21) Appl. No.: 13/169,281

(22) Filed: Jun. 27, 2011

(65) Prior Publication Data

US 2011/0319581 A1 Dec. 29, 2011

(30) Foreign Application Priority Data

Jun. 28, 2010 (JP) .................. 2010-146251

(51) Int. Cl.
C08G 77/24 (2006.01)

(52) U.S. Cl.
USPC .................. 528/15; 528/31; 528/42; 556/445; 556/448

(58) Field of Classification Search
USPC .................. 528/15, 31, 42; 554/445, 448
See application file for complete search history.

(56) References Cited

U.S. PATENT DOCUMENTS

| | | | |
|---|---|---|---|
| 7,488,839 B2 | 2/2009 | Yamaguchi et al. | |
| 2008/0071042 A1 | 3/2008 | Yamane et al. | |

FOREIGN PATENT DOCUMENTS

| | | | |
|---|---|---|---|
| EP | 1 724 332 A1 | 11/2006 | |
| EP | 2 196 488 | * | 6/2010 |
| EP | 2 196 488 A1 | 6/2010 | |
| JP | 59-22611 | 2/1984 | |
| JP | 60-22907 | 2/1985 | |
| JP | 2006-321764 | 11/2006 | |
| JP | 2008-88412 | 4/2008 | |
| JP | 2008-308628 | 12/2008 | |

OTHER PUBLICATIONS

Extended Search Report issued in Sep. 29, 2011 in European Patent Application No. 11171513.2-1214.

* cited by examiner

Primary Examiner — Margaret Moore
(74) Attorney, Agent, or Firm — Oblon, Spivak, McClelland, Maier & Neustadt, L.L.P.

(57) ABSTRACT

A polyether-modified polysiloxane containing a perfluoropolyether group and its production method are provided. The polysiloxane has both the properties of a perfluoropolyether and the properties of a polyether-modified silicone, and it also has high affinity for organic solvents as well as coating compositions, cosmetics, and various coating materials. The polysiloxane is represented by the following general formula (1):

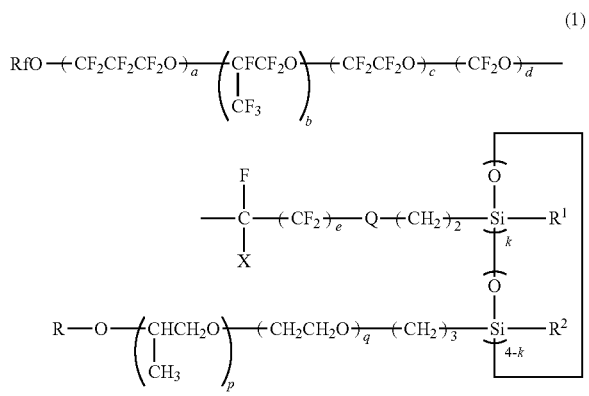

wherein Rf is a perfluoroalkyl group; X is fluorine atom or trifluoromethyl group; Q is a divalent organic group, R is hydrogen atom, an alkyl group, or acyl group; $R^1$ and $R^2$ are an alkyl group, aryl group, or an aralkyl group; a, b, c, d are 0 to 200; a+b+c+d is at least 1; e is 0 or 1; p and q are 0 to 50 with the proviso that p+q is at least 2; and k is 1 to 3.

4 Claims, 1 Drawing Sheet

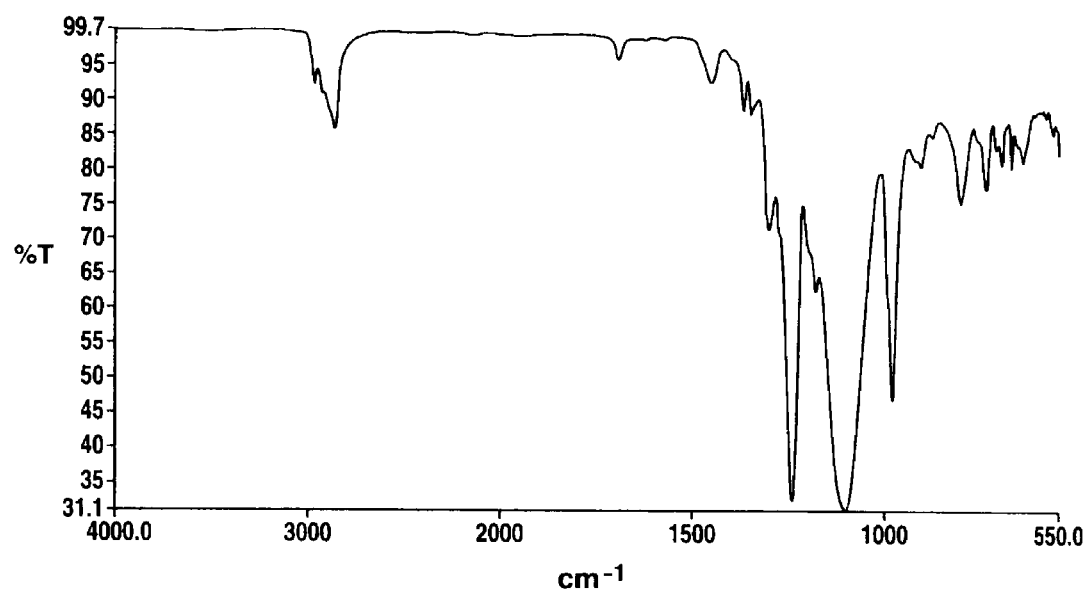

POLYETHER-MODIFIED POLYSILOXANE CONTAINING A PERFLUOROPOLYETHER GROUP AND ITS PRODUCTION METHOD

CROSS-REFERENCE TO RELATED APPLICATION

This non-provisional application claims priority under 35 U.S.C. §119(a) on Patent Application No. 2010-146251 filed in Japan on Jun. 28, 2010, the entire contents of which are hereby incorporated by reference.

TECHNICAL FIELD

This invention relates to a novel polyether-modified polysiloxane containing a perfluoropolyether group which has both the properties of a perfluoropolyether and the properties of a polyether-modified silicone, and which has a high leveling property due to the high affinity for organic solvents, coating compositions, cosmetics, and various coating materials.

BACKGROUND ART

Perfluoropolyether group-containing compounds generally have extremely low surface energy, and hence, they have unique properties such as water and oil repellency, chemical resistance, lubricity, mold releasability, anti-fouling properties. Because of such properties, the perfluoropolyether group-containing compounds have been used as a water and oil-repellant anti-fouling agent for papers and fibers, a lubricant for a magnetic recording medium, a grease-proof agent for precision machines, a mold release agent, cosmetics, protective films, and the like. However, the low surface energy of the perfluoropolyether group-containing compound also means that this compound has extremely low compatibility and affinity for organic solvents as well as substances such as coating composition, cosmetics, and various coating materials, and accordingly, it has been pointed out that, when the perfluoropolyether group-containing compound is added to various industrial materials to thereby impart the materials with the properties as described above, the mixture suffered from insufficient dispersion stability and the like to result in the difficulty of blending.

In the meanwhile, polysiloxane compounds (silicones) also have low surface energy, and hence, the properties such as water repellency, lubricity, and releasability. The polysiloxane compounds, however, have higher affinity for organic solvents as well as coating compositions, cosmetics, and various coating materials compared to the perfluoropolyether compound, and their dispersion stability can be improved by various types of modification. More specifically, a silicone modified with a polyether chain such as polyethylene glycol or polypropylene glycol is well adapted for use as a nonionic surfactant in applications such as a starting material for cosmetics, foam regulator in urethane foam, additive in the plastics, anti-fogging agent, anti-foaming agent, textile treatment agent, and water-soluble lubricant since the polysiloxane chain functions as a hydrophobic group and the polyether group functions as a hydrophilic group.

Perfluoropolyether-modified polysiloxane compounds have been synthesized as a compound having both the perfluoropolyether group and the polysiloxane chain. (JP-A 2006-321764, JP-A 2008-308628, JP-A 2008-88412, JP-A 59-22611, and JP-A 60-22907).

However, when the degree of fluorine modification is increased to thereby improve the properties inherent to the perfluoropolyether group, the compound suffers from drastically reduced affinity for other materials, and hence, the compound suffers from the problems such as dispersion stability. Accordingly, there is a demand for the development of a compound which has both the properties of the perfluoropolyether and the properties of the polyether-modified silicone, and which has high affinity for organic solvents as well as coating compositions, cosmetics, and various coating materials.

SUMMARY OF THE INVENTION

In view of the situation as described above, an object of the present invention is to provide a compound which has both the properties of a perfluoropolyether and the properties of a polyether-modified silicone, and which has high affinity for organic solvents as well as coating compositions, cosmetics, and various coating materials. Another object of the present invention is to provide a method for producing such compound.

The inventors of the present invention conducted an intensive study to obviate the problems as described above, and found that a novel polyether-modified polysiloxane containing a perfluoropolyether group represented by the following general formula (1) has both the properties of the perfluoropolyether and the properties of the polyether-modified silicone, and also, a high affinity for organic solvents as well as coating compositions, cosmetics, and various coating materials. The present invention has been completed on the bases of such finding.

Accordingly, the present invention provides a polyether-modified polysiloxane containing a perfluoropolyether group as described below. The present invention also provides its production method.

[1] A polyether-modified polysiloxane containing a perfluoropolyether group represented by the following general formula (1):

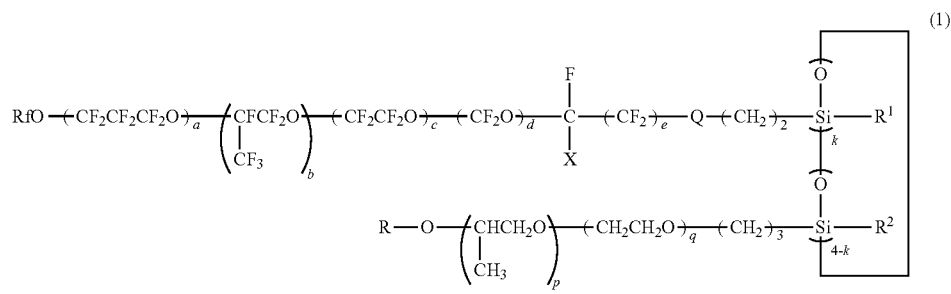

wherein Rf represents a straight chain or branched perfluoroalkyl group containing 1 to 10 carbon atoms; X represents fluorine atom or trifluoromethyl group; Q represents a divalent organic group containing 1 to 12 carbon atoms; R represents hydrogen atom, or an alkyl group or acyl group containing 1 to 6 carbon atoms; $R^1$ and $R^2$ are independently an alkyl group, aryl group, or an aralkyl group containing 1 to 10 carbon atoms; a, b, c, d are independently an integer of 0 to 200 with the proviso that a+b+c+d is at least 1; e is 0 or 1; p and q are independently an integer of 0 to 50 with the proviso that p+q is at least 2; and k is an integer of 1 to 3.

[2] A polyether-modified polysiloxane containing a perfluoropolyether group according to the above [1] represented by the following general formula (2):

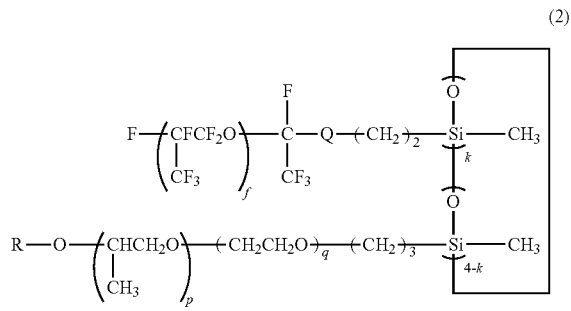

(2)

wherein Q, R, p, q, p+q, and k are as described above, and f is an integer of 2 to 200.

[3] A polyether-modified polysiloxane containing a perfluoropolyether group according to the above [1] or [2] wherein content of the fluorine atom by weight in the molecule is in the range of 20 to 70% by weight.

[4] A method for producing a polyether-modified polysiloxane containing a perfluoropolyether group according to any one of the above [1] to [3] comprising steps of reacting a vinyl group-containing perfluoropolyether represented by the following general formula (3):

wherein Rf, X, Q, a, b, c, d, a+b+c+d, and e are as described above with a tetraorganocyclotetrasiloxane for hydrosilylation to produce a perfluoropolyether-modified cyclotetrasiloxane; and reacting the perfluoropolyether-modified cyclotetrasiloxane with an allyl group-containing polyether compound represented by the following general formula (4):

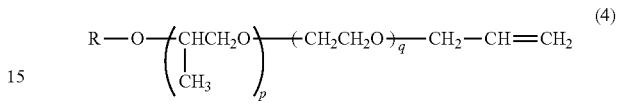

(4)

wherein R, p, q, and p+q are as described above for hydrosilylation to produce the polyether-modified polysiloxane containing a perfluoropolyether group.

ADVANTAGEOUS EFFECTS OF THE INVENTION

Accordingly, the present invention provides a polyether-modified polysiloxane containing a perfluoropolyether group which has both the properties of a perfluoropolyether and the properties of a polyether-modified silicone, and which has high leveling property due to the high affinity for organic solvents, coating compositions, cosmetics, and various coating materials.

BRIEF DESCRIPTION OF THE DRAWING

FIG. 1 is an IR spectrum of the compound prepared in Example 1.

DETAILED DESCRIPTION OF THE INVENTION

Next, the present invention is described in detail.

As described above, the polyether-modified polysiloxane containing a perfluoropolyether group of the present invention is represented by the following general formula (1):

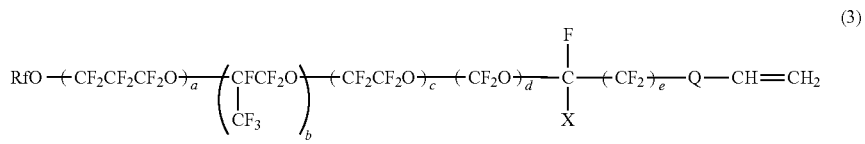

(3)

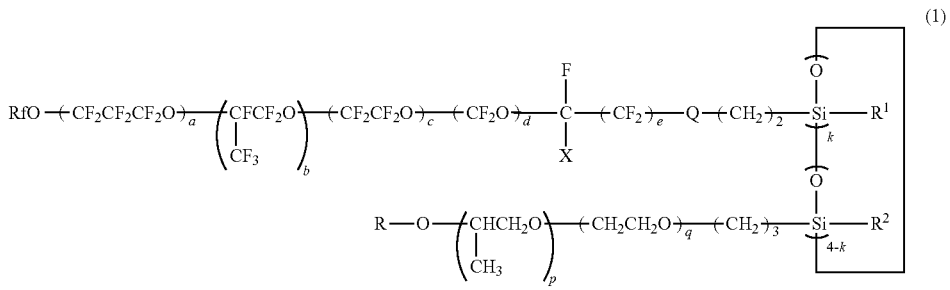

In the general formula (1), Rf represents a straight chain or branched perfluoroalkyl group containing 1 to 10 carbon atoms, and preferably 1 to 3 carbon atoms. When the number of carbon atoms in the Rf exceeds such range, the perfluoropolyether chain may have an insufficient flexibility, and generation of toxic perfluorooctanoic acid (PFOA) may be induced in the course of thermal decomposition.

Examples of such perfluoroalkyl group Rf include the groups represented by the following formulae:

$CF_3-$, $CF_3CF_2-$, $CF_3CF_2CF_2-$, $(CF_3)_2CF-$, and $(CF_3)_2CFCF_2-$.

In the formula (1), Q is a divalent organic group containing 1 to 12 carbon atoms, and preferably 3 to 8 carbon atoms. Exemplary such groups include alkylene groups such as methylene group, ethylene group, propylene group (trimethylene group or methylethylene group), butylene group (tetramethylene group or methylpropylene group), hexamethylene group, and octamethylene group; arylene group such as phenylene group; and combination of two or more such groups (for example, an alkylene-arylene group). Examples also include any of these groups bonded to at least one structure selected from ether bond, amide bond, ester bond, diorganosylilene group, and the like as well as divalent hydrocarbon groups optionally containing at least one member selected from oxygen atom, nitrogen atom, and silicon atom.

Examples of such Q include groups represented by the following formulae:

$-CH_2-$, $-CH_2CH_2-$, $-(CH_2)_n-O-CH_2-$, $-OCH_2-$, $-CO-NH-CH_2-$, $-CO-N(Ph)-CH_2-$, $-CO-NH-CH_2CH_2-$, $-CO-N(Ph)-CH_2CH_2-$, $-CO-N(CH_3)-CH_2CH_2CH_2-$, $-CO-O-CH_2-$, $-CO-N(CH_2)-Ph'-$, $-CO-NR^3-Y'-$ wherein, Ph is phenyl group, Ph' is phenylene group, n is an integer of 1 to 10, Y' is $-CH_2-$ or a divalent group represented by the following formula:

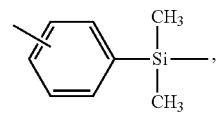

$R^3$ is hydrogen atom or an unsubstituted or substituted monovalent hydrocarbon group preferably containing 1 to 10 carbon atoms.

In the formula (1), R is hydrogen atom or an alkyl group or acyl group containing 1 to 6 carbon atoms such as methyl group, ethyl group, n-butyl group, and acetyl group. Among these, the preferred are methyl group, n-butyl group, and acetyl group.

In the formula (1), $R^1$ and $R^2$ are independently an alkyl group, an aryl group, or an aralkyl group containing 1 to 10 carbon atoms such as methyl group, ethyl group, isopropyl group, n-butyl group, isobutyl group, cyclohexyl group, phenyl group, benzyl group, phenylethyl group, and 2-phenyl propyl group. Of these, the preferred are methyl group, n-butyl group, and phenyl group, and the most preferred is methyl group. With regard to $R^1$ and $R^2$, each of $R^1$ and $R^2$ may be the same or different group, and $R^1$ and $R^2$ may be the same or different.

In the formula (1), X is fluorine atom or trifluoromethyl group.

In the formula (1), a, b, c, and d are independently an integer of 0 to 200, and preferably 20 to 100 with the proviso that a+b+c+d is at least 1, preferably 2 to 200, more preferably 3 to 100, and most preferably 5 to 50, e is 0 or 1, p and q are independently an integer of 0 to 50, and preferably 0 to 30, with the proviso that p+q is at least 2, preferably 3 to 50, more preferably 6 to 40, and most preferably 9 to 30, and k is an integer of 1 to 3, preferably 1 or 2, and most preferably 1.

Content of the perfluoropolyether chain and the polyether chain in the compound of the formula (1) is preferably such that the fluorine atoms in the molecule is 20 to 70%, and more preferably 25 to 55% by weight of the molecule. When the content is less than such range, the desired properties are less likely to be realized and the compound is less likely to have the water and oil repellency, lubricity, and mold releasability inherent to the perfluoropolyether chain. When the content is in excess of such range, the compound may suffer from insufficient affinity for other materials.

In view of the availability of the starting materials and ease of the production, the polyether-modified polysiloxane containing a perfluoropolyether group represented by the general formula (1) is preferably a polyether-modified polysiloxane containing a perfluoropolyether group having the structure represented by the following general formula (2):

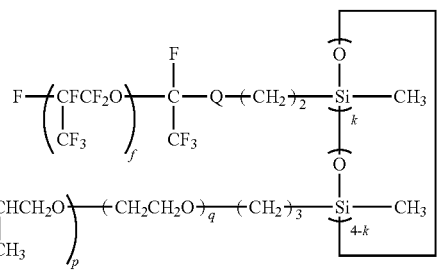

(2)

wherein Q, R, p, q, p+q, and k are as described above, f is an integer of 2 to 200, preferably 3 to 50, and more preferably 4 to 40.

Examples of the polyether-modified polysiloxane containing a perfluoropolyether group of the present invention include those as represented by the following formulae.

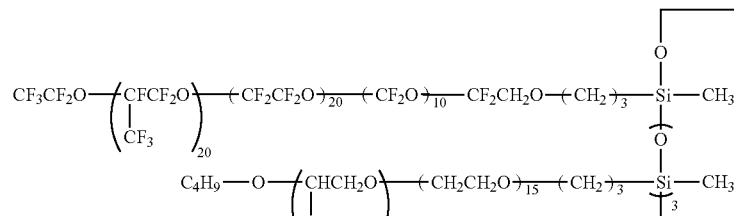

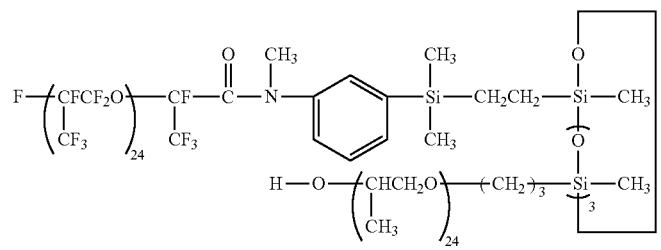

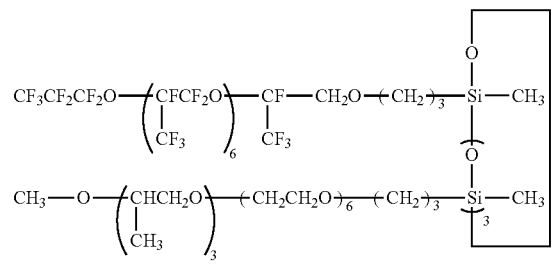

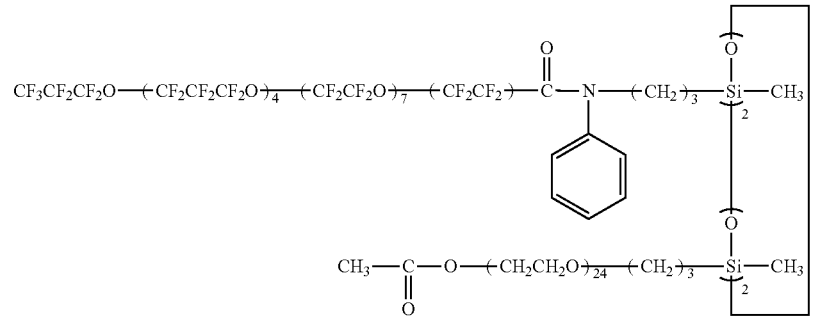

-continued

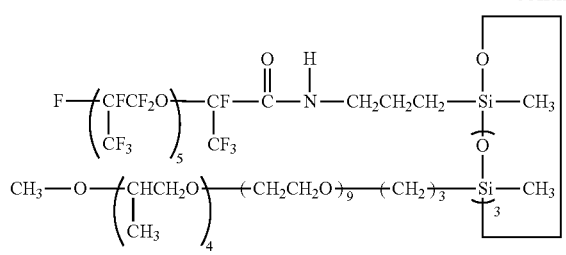

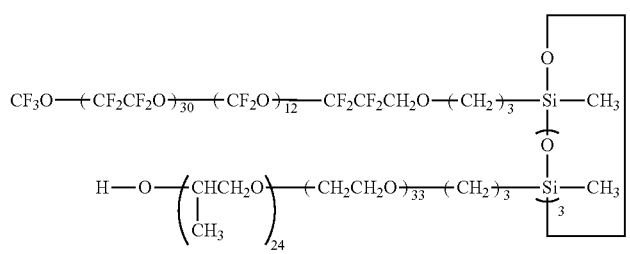

Production Method of the Polyether-Modified Polysiloxane Containing a Perfluoropolyether Group The polyether-modified polysiloxane containing a perfluoropolyether group of the present invention can be produced by promoting hydrosilylation between a vinyl group-containing perfluoropolyether represented by the following general formula (3) and a tetraorganocyclotetrasiloxane preferably in the presence of a platinum catalyst to thereby produce a perfluoropolyether-modified cyclotetrasiloxane, and further promoting hydrosilylation between the resulting perfluoropolyether-modified cyclotetrasiloxane and an allyl group-containing polyether compound represented by the general formula (4) preferably in the presence of a platinum catalyst to thereby produce the polyether-modified polysiloxane containing a perfluoropolyether group.

In other words, the production of the polyether-modified polysiloxane containing a perfluoropolyether group of the present invention is accomplished by a process comprising the following two stages.

<First Stage Reaction>

In the first stage reaction, the vinyl group in the vinyl group-containing perfluoropolyether (i) represented by the following general formula (3):

wherein Rf, X, Q, a, b, c, d, a+b+c+d, and e are as described above is partially hydrosilylated by addition with the 4 SiH groups in the tetraorganocyclotetrasiloxane (ii) represented by the following formula:

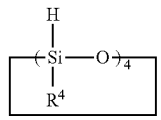

wherein $R^4$ is independently, an alkyl group, an aryl group, or an aralkyl group containing 1 to 10 carbon atoms which may be the same as the one mentioned for the $R^1$ and $R^2$ preferably in the presence of a platinum catalyst to thereby produce a perfluoropolyether-modified cyclotetrasiloxane containing SiH group (iii) represented by the following general formula:

(3)

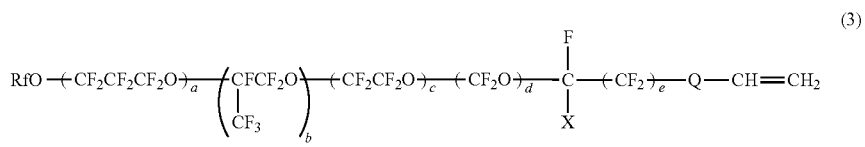

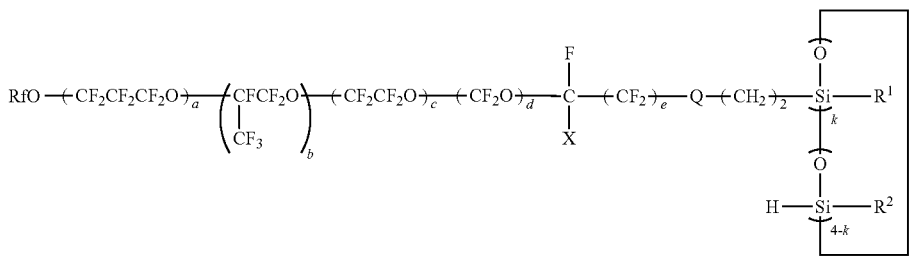

wherein Rf, X, Q, $R^1$, $R^2$, a, b, c, d, a+b+c+d, e, and k are as described above having 1 to 3, and preferably 1 or 2 perfluoropolyether-modified siloxane units per molecule, and also having the SiH group remaining in the molecule.

<Second Stage Reaction>

Next, the SiH group remaining in the perfluoropolyether-modified cyclotetrasiloxane containing SiH group (iii) and the allyl group in the allyl group-containing polyether compound (iv) represented by the general formula (4):

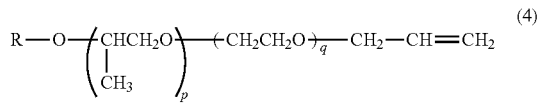

wherein R, p, q, and p+q are as described above is allowed to undergo partial hydrosilylation by addition preferably in the presence of a platinum catalyst to thereby produce the polyether-modified polysiloxane containing a perfluoropolyether group (v) represented by the general formula (1).

In the first stage reaction of the two stage production as described above, namely, in the reaction between the vinyl group-containing perfluoropolyether (i) and the tetraorganocyclotetrasiloxane (ii), the molar ratio between the molecules, namely, [the siloxane (ii)]/[the perfluoropolyether (i)] is preferably at least 2.0, and more preferably at least 3.0. Such excessive use of the tetraorganocyclotetrasiloxane (namely, the molar ratio≧2.0) enables preferential production of the perfluoropolyether-modified cyclotetrasiloxane of the general formula (1) wherein k=1. While there is no upper limit for the molar ratio, the molar ratio is preferably up to about 10.0, and more preferably up to about 5.0 in view of the production efficiency (such as yield of the target product and the like). As described above, k=1 is the most preferable value in the present invention to realize the structure of the polysiloxane of the present invention wherein the surface activity is its highest. The excessive tetraorganocyclotetrasiloxane can be readily removed after the completion of the reaction by distillation under reduced pressure.

In the second stage reaction of the two stage production as described above, namely, in the reaction between the perfluoropolyether-modified cyclotetrasiloxane containing SiH group (iii) and the allyl group-containing polyether compound (iv), molar ratio of the SiH group in the perfluoropolyether-modified cyclotetrasiloxane containing SiH group (iii) to the allyl group in the allyl group-containing polyether compound (iv) (SiH/allyl ratio) is preferably in the range of 0.8 to 1.2, more preferably 0.9 to 1.1, and most preferably 0.9 to 1.0. The SiH group in the cyclotetrasiloxane in excess of such range may result in an insufficient affinity of the resulting compound with other materials, and generation of hydrogen gas by dehydrogenation of the SiH group. On the other hand, the allyl group in the polyether compound in excess of such range may result in the loss of properties inherent to the perfluoropolyether.

In addition, when this production process is conducted not by the two stage reaction process as described above but by reacting the vinyl group-containing perfluoropolyether (i) of the formula (3), the tetraorganocyclotetrasiloxane (ii), and the allyl group-containing polyether compound (iv) of the formula (4) at once, a cyclotetrasiloxane modified only by the vinyl group-containing perfluoropolyether (i) or the allyl group-containing polyether compound (iv) may be formed due to the difference in the reactivity with the SiH group of the vinyl group-containing perfluoropolyether (i) and the allyl group-containing polyether compound (iv); or generation of various types of compounds each modified by the vinyl group-containing perfluoropolyether (i) and the allyl group-containing polyether compound (iv) at different modification degree may take place, leading to turbidity of the resulting product.

The platinum catalyst used in the production process as described above may be a known catalyst which has been used in the hydrosilylation. Since such catalysts are typically a precious metal compound which is expensive, the catalysts commonly used in the hydrosilylation are platinum and platinum compounds which are relatively readily available. Examples of such platinum compound include chloroplatinic acid and a complex of chloroplatinic acid with an olefin such as ethylene; a complex of chloroplatinic acid with an alcohol or vinyl siloxane; and metal platinum supported on silica, alumina, carbon, or the like. Examples of the Platinum Group metal catalyst other than the platinum compounds include rhodium, ruthenium, iridium, and palladium compounds such as $RhCl(PPh_3)_3$, $RhCl(CO(PPh_3)_2$, $Ru_3(CO)_{12}$, $IrCl(CO)(PPh_3)_2$, and $Pd(PPh_3)_4$ wherein Ph represents phenyl group.

The platinum catalyst may be used at a catalytic amount, and more specifically, at 0.1 to 500 ppm (in terms of the weight of the platinum) in relation to the total amount of the vinyl group-containing perfluoropolyether (i) and the tetraorganocyclotetrasiloxane (ii), or the total amount of the perfluoropolyether-modified cyclotetrasiloxane containing SiH group (iii) and the allyl group-containing polyether compound (iv).

If desired, the hydrosilylation reaction may be conducted by using a solvent. For both the first and second stage reactions, the solvent is preferably the one which is capable of dissolving both reaction materials in each stage of the reaction. The solvent, however, may be the one which only dissolves one of the reaction materials, and the solvent is not particularly limited as long as it does not inhibit the hydrosilylation reaction.

Exemplary such solvents include aliphatic hydrocarbon compounds such as n-hexane, n-heptane, isooctane, and isododecane; aromatic hydrocarbon compounds such as toluene and xylene; fluorine-containing aromatic hydrocarbon compounds such as trifluorotoluene and hexafluoro-m-xylene; hydrofluoroether compounds such as perfluorobutylmethyl ether, perfluorobutylethyl ether, and 1,1,1,2,2,3,4,5,5,5-decafluoro-3-methoxy-4-(trifluoromethyl)pentane; chlorofluorocarbon compounds such as difuroyl (manufactured by Daikin Industries, Ltd.); and perfluoropolyether compounds such as FOMBLIN and GALDEN (manufactured by Solvay Solexis), DEMNUM (manufactured by Daikin Industries, Ltd.), and Krytox (manufactured by DuPont). Among these, the preferred is hexafluoro-m-xylene in view of its high capability of dissolving the vinyl group-containing perfluoropolyether (i) of the formula (3), the perfluoropolyether-modified cyclotetrasiloxane containing SiH group (iii), the allyl group-containing polyether compound (iv) of the formula (4), and the final product (the polyether-modified polysiloxane containing a perfluoropolyether group (v) of the formula (1).

Amount of the solvent used may be adequately selected depending on the amount and viscosity of each reaction material. The solvent, however, is preferably used at 10 to 200 parts by weight, and more preferably at 20 to 100 parts by weight per 100 parts by weight of the total of reaction materials.

The reaction temperature used in the production process as described above may be adequately selected depending on the amount and type of the solvent, and the preferable temperature is typically in the range of room temperature (25° C.) to 140° C., and preferably 70 to 120° C. The temperature in excess of such range is not preferable since use of such temperature may result in thermal decomposition of the polyether chain and the cyclic siloxane chain. The reaction time is not particularly limited, and the reaction time may be adequately selected depending on the respective reaction conditions so that the reaction proceeds to a sufficient degree.

The polyether-modified polysiloxane containing a perfluoropolyether group of the present invention has an excellent water and oil repellency, chemical resistance, lubricity, and mold releasability, as well as an improved affinity for organic solvents, coating composition, cosmetics, various coating materials, and other materials over the conventional perfluoropolyether group-containing compounds. Accordingly, the polyether-modified polysiloxane containing a perfluoropolyether group of the present invention is well adapted for use as an additive in cosmetics, a foam regulator in urethane foam, a mold release agent for improving releasability from a metal mold in the molding, an additive for imparting water and oil repellency with greases, an additive for improving abrasion resistance of a lubricant oil, an agent for improving coloring and dispersion property of pigment in the field of dye and pigment industry, or an agent for improving leveling and anti-cratering property to thereby reduce coating defects.

EXAMPLES

Next, the present invention is described in further detail by referring to the following Examples, Comparative Examples, Use Examples, and Comparative Use Examples, which by no means limit the scope of the invention.

Example 1

A flask equipped with a reflux condenser and a thermometer was charged with 96.2 g of 1,3,5,7-tetramethylcyclotetrasiloxane and 105.7 g of hexafluoro-m-xylene, and a dropping funnel was charged with a mixed solution of 432.2 g of vinyl group-containing perfluoropolyether represented by the following formula (5):

(5)

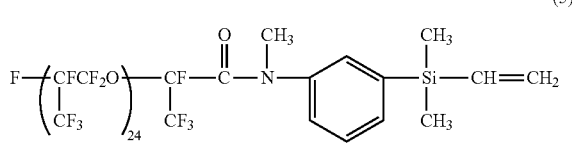

([siloxane]/[perfluoropolyether]=4.0 (molar ratio)), 0.32 g of a solution of platinum-vinyl siloxane complex in toluene (an amount containing 1.6 mg of platinum), and 52.8 g of hexafluoro-m-xylene. After heating to an internal temperature of 80° C., the solution was added at an internal temperature 110° C. After heating to 90 to 100° C. for 1 hour and confirming the disappearance of the peak from the vinyl group of the perfluoropolyether (5) by IR spectrum, the hexafluoro-m-xylene and excessive cyclotetrasiloxane were removed by distillation at a reduced pressure to obtain 455.2 g of SiH group-containing cyclotetrasiloxane modified with perfluoropolyether represented by the following formula (6).

(6)

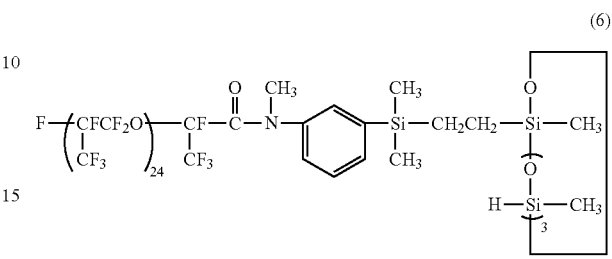

Next, 150.0 g of the thus obtained cyclotetrasiloxane (6) and 146.9 g of hexafluoro-m-xylene were added to a flask equipped with a reflux condenser and a thermometer, and after heating to an internal temperature of 80° C., 0.18 g of a solution of platinum-vinyl siloxane complex in toluene (an amount containing 0.9 mg of platinum) was added, and 143.8 g of an allyl group-containing polyether compound represented by the following formula (7):

(7)

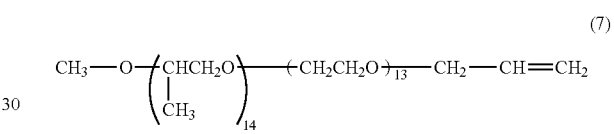

(SiH group in the siloxane (6)/allyl group in the polyether compound (7)=0.95 (molar ratio)) was added dropwise at 80 to 90° C. After the completion of the dropwise addition, and heating to 80° C. for 1 hour, the hexafluoro-m-xylene was removed by distillation at a reduced pressure to obtain 290.8 g of a white paste product.

The resulting product was analyzed by $^1$H-NMR and IR spectrum measurement, and the product was found to be a compound represented by the following formula (8):

(8)

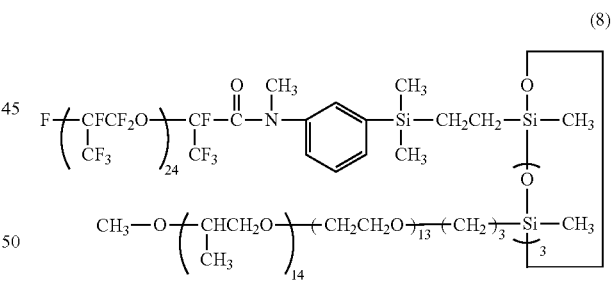

having a fluorine atom content by weight in the molecule of 31.7%. This compound was used in Use Example 1.

The result of the $^1$H-NMR (using JNM-NS50 manufactured by JEOL) is described below.

$^1$H-NMR (TMS standard, ppm): 0.0-0.1 (≡Si—CH$_3$, 18H), 0.1-0.2 (≡Si—CH$_2$—, 10H), 1.0-1.3 (—CH$_3$, 126H), 1.5-1.7 (—CH$_2$—, 6H), 3.3-3.8 (CH$_3$—O—, —CH$_2$—O—, —CH—O—, —NCH$_3$, 300H), 7.2-7.7 (—C$_6$H$_4$—, 4H)

IR spectrum of the compound (measured by KBr method using FT-730 manufactured by HORIBA, Ltd.) is shown in FIG. 1.

Example 2

A flask equipped with a reflux condenser and a thermometer was charged with 96.2 g of 1,3,5,7-tetramethylcyclotetrasiloxane and 106.1 g hexafluoro-m-xylene, and a dropping funnel was charged with a mixed solution of 434.1 g of vinyl group-containing perfluoropolyether represented by the following formula (9):

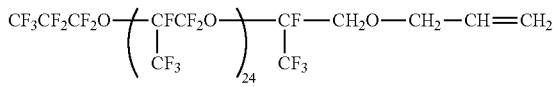
(9)

([siloxane]/[perfluoropolyether]=4.0 (molar ratio)), 0.32 g of a solution of platinum-vinyl siloxane complex in toluene (an amount containing 1.6 mg of platinum), and 53.0 g of hexafluoro-m-xylene. After heating to an internal temperature of 80° C., the solution was added at an internal temperature 110° C. After heating to 90 to 100° C. for 1 hour and confirming the disappearance of the peak from the allyl group of the perfluoropolyether (9) by IR spectrum, the hexafluoro-m-xylene and excessive cyclotetrasiloxane were removed by distillation at a reduced pressure to obtain 456.3 g of SiH group-containing cyclotetrasiloxane modified with perfluoropolyether represented by the following formula (10).

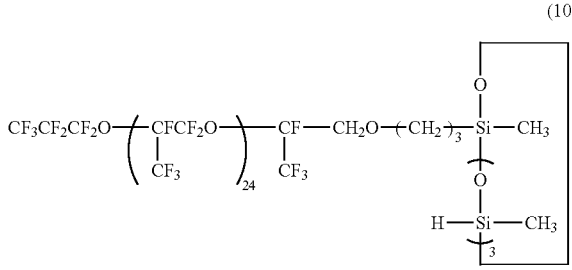
(10)

Next, 150.0 g of the thus obtained cyclotetrasiloxane (10) and 112.5 g of hexafluoro-m-xylene were added to a flask equipped with a reflux condenser and a thermometer, and after heating to an internal temperature of 80° C., 0.18 g of a solution of platinum-vinyl siloxane complex in toluene (an amount containing 0.9 mg of platinum) was added, and 75.0 g of an allyl group-containing polyether compound represented by the following formula (11):

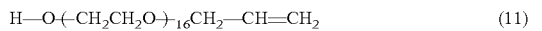
(11)

(SiH group in the siloxane (10)/allyl group in the polyether compound (11)=0.95 (molar ratio)) was added dropwise at 80 to 90° C. After the completion of the dropwise addition, and heating to 80° C. for 1 hour, the hexafluoro-m-xylene was removed by distillation at a reduced pressure to obtain 224.0 g of a white paste product.

The resulting product was analyzed by $^1$H-NMR and IR spectrum measurement, and the product was found to be a compound represented by the following formula (12):

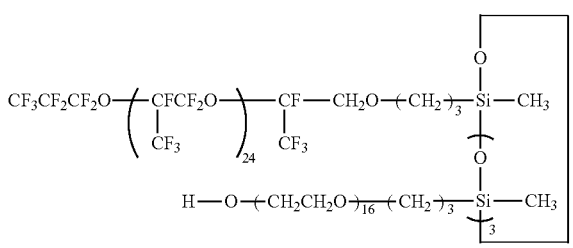
(12)

having a fluorine atom content by weight in the molecule of 42.9%. This compound was used in Use Example 2.

Example 3

A flask equipped with a reflux condenser and a thermometer was charged with 96.2 g of 1,3,5,7-tetramethylcyclotetrasiloxane and 39.9 g of hexafluoro-m-xylene, and a dropping funnel was charged with a mixed solution of 103.3 g of allyl group-containing perfluoropolyether represented by the following formula (13):

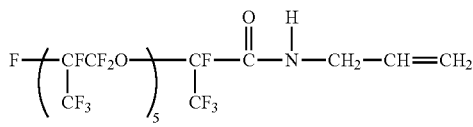
(13)

([siloxane]/[perfluoropolyether]=4.0 (molar ratio)), 0.32 g of a solution of platinum-vinyl siloxane complex in toluene (an amount containing 1.6 mg of platinum), and 20.0 g of hexafluoro-m-xylene. After heating to an internal temperature of 80° C., the solution was added at an internal temperature 110° C. After heating to 90 to 100° C. for 1 hour and confirming the disappearance of the peak from the allyl group of the perfluoropolyether (13) by IR spectrum, the hexafluoro-m-xylene and excessive cyclotetrasiloxane were removed by distillation at a reduced pressure to obtain 127.3 g of SiH group-containing cyclotetrasiloxane modified with perfluoropolyether represented by the following formula (14).

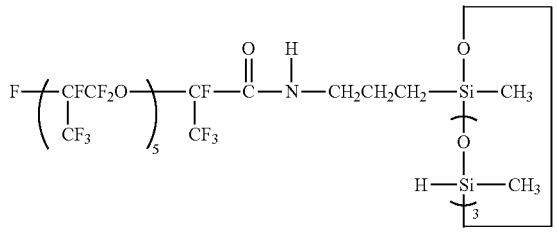
(14)

Next, 100.0 g of the thus obtained cyclotetrasiloxane (14) and 109.0 g of hexafluoro-m-xylene were added to a flask equipped with a reflux condenser and a thermometer, and after heating to an internal temperature of 80° C., 0.18 g of a solution of platinum-vinyl siloxane complex in toluene (an amount containing 0.9 mg of platinum) was added, and 118.0 g of an allyl group-containing polyether compound represented by the following formula (15):

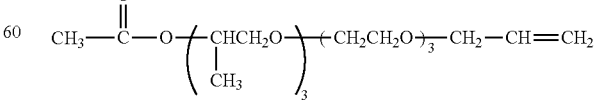
(15)

(SiH group in the siloxane (10)/allyl group in the polyether compound (11)=0.95 (molar ratio)) was added dropwise at 80 to 90° C. After the completion of the dropwise addition, and heating to 80° C. for 1 hour, the hexafluoro-m-xylene was removed by distillation at a reduced pressure to obtain 216.9 g of a pale brown oily product.

The resulting product was analyzed by ¹H-NMR and IR spectrum measurement, and the product was found to be a compound represented by the following formula (16):

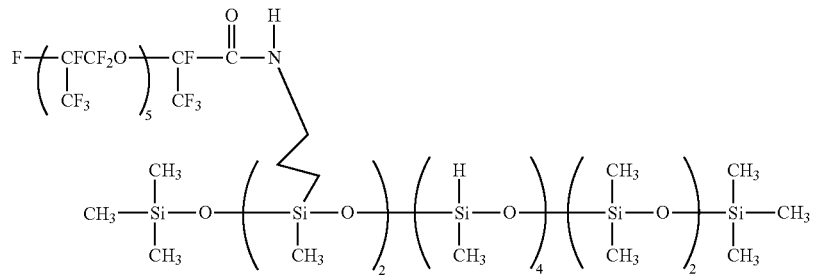

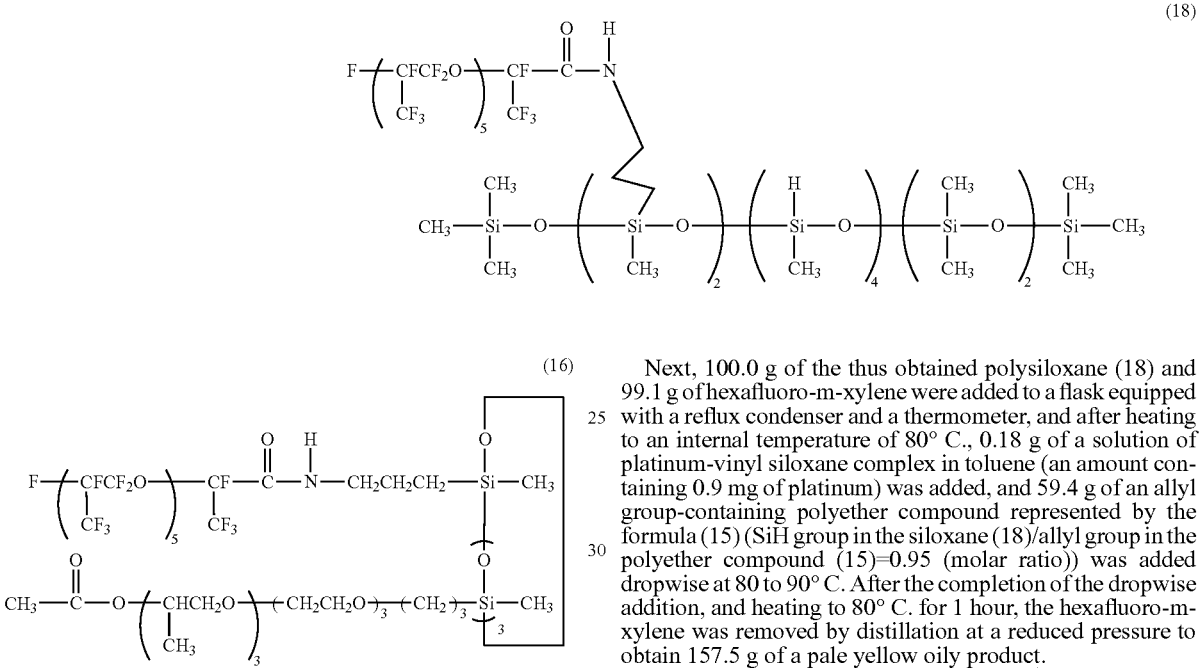

having a fluorine atom content by weight in the molecule of 26.7%. This compound was used in Use Example 3.

([siloxane]/[perfluoropolyether]=0.5 (molar ratio)), and 54.8 g of hexafluoro-m-xylene. After adding 0.45 g of a solution of platinum-vinyl siloxane complex in toluene (corresponding to 2.3 mg of Pt), and heating to a temperature of 80° C. for 1 hour, the hexafluoro-m-xylene was removed by distillation at a reduced pressure to obtain 271.3 g of SiH group-containing polysiloxane modified with perfluoropolyether represented by the following formula (18).

Next, 100.0 g of the thus obtained polysiloxane (18) and 99.1 g of hexafluoro-m-xylene were added to a flask equipped with a reflux condenser and a thermometer, and after heating to an internal temperature of 80° C., 0.18 g of a solution of platinum-vinyl siloxane complex in toluene (an amount containing 0.9 mg of platinum) was added, and 59.4 g of an allyl group-containing polyether compound represented by the formula (15) (SiH group in the siloxane (18)/allyl group in the polyether compound (15)=0.95 (molar ratio)) was added dropwise at 80 to 90° C. After the completion of the dropwise addition, and heating to 80° C. for 1 hour, the hexafluoro-m-xylene was removed by distillation at a reduced pressure to obtain 157.5 g of a pale yellow oily product.

The resulting product was analyzed by ¹H-NMR and IR spectrum measurement, and the product was found to be a compound represented by the following formula (19):

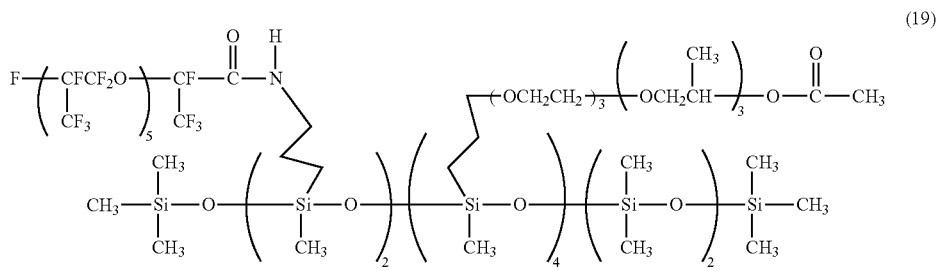

having a fluorine atom content by weight in the molecule of 30.5%. This compound was used in Comparative Use Example 2.

Comparative Example 1

A flask equipped with a reflux condenser and a thermometer was charged with 206.7 g of the allyl group-containing perfluoropolyether represented by the formula (13), 67.2 g of SiH group-containing polysiloxane represented by the following formula (17):

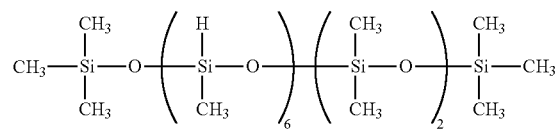

Use Examples 1 to 3

A transparent glass sample bottle was charged with 4.0 g of the polyether-modified polysiloxane containing a perfluoropolyether group produced in Examples 1 to 3 and 16.0 g of the solvent shown in Table 1, and the mixture was thoroughly shaken. After allowing to stand at room temperature for 1 hour, outer appearance was visually examined to evaluate solubility in the solvents by the following criteria. The results are shown in Table 1.

○: the polysiloxane dissolved, giving a transparent solution.

Δ: the polysiloxane homogeneously dispersed giving a white semi-transparent dispersion.

x: two separate layers, namely, the layer of white turbid layer or the siloxane and the layer of solvent are separated.

Comparative Use Examples 1 to 3

The procedure of the Use Example was repeated by using the compounds as described below instead of the compounds of the Examples 1 to 3 to evaluate solubility of the polysiloxane in each solvent. The results are also shown in Table 1.

Comparative Use Example 1

Polydimethylsiloxane (KF-96 manufactured by Shin-Etsu Chemical Co., Ltd.) having a viscosity at 25° C. of 200 mm²/s.

Comparative Use Example 2

The polyether-modified polysiloxane containing a perfluoropolyether group of formula (19) produced in Comparative Example 1.

Comparative Use Example 3

Perfluoropolyether oligomer (PFPE) (Galden HT-200 manufactured by Solvay Solexis).

TABLE 1

|  | Solvent | | | | | |
|---|---|---|---|---|---|---|
|  | THF | IPA | MIBK | Iso-dodecane | Ethyl acetate | MXHF |
| Use Example 1 | ◯ | ◯ | ◯ | ◯ | ◯ | ◯ |
| Use Example 2 | ◯ | Δ | ◯ | ◯ | ◯ | ◯ |
| Use Example 3 | ◯ | ◯ | ◯ | ◯ | ◯ | ◯ |
| Comparative Use Example 1 | ◯ | X | ◯ | ◯ | ◯ | X |
| Comparative Use Example 2 | ◯ | X | ◯ | Δ | X | ◯ |
| Comparative Use Example 3 | X | X | X | X | X | ◯ |

THF: tetrahydrofuran
IPA: isopropanol
MIBK: methyl isobutyl ketone
MXHF: m-xylenehexafluoride The results shown in Table 1 demonstrate that the polyether-modified polysiloxane containing a perfluoropolyether group of the present invention is superior in the solubility and the affinity for many organic solvents compared to the compounds used in the Comparative Use Examples 1 to 3.

As described above, the polyether-modified polysiloxane containing a perfluoropolyether group of the present invention is well adapted for use as an additive in cosmetics, a foam regulator in urethane foam, a mold release agent for improving releasability from a metal mold in the molding, an additive for imparting water and oil repellency with greases, an additive for improving abrasion resistance of a lubricant oil, an agent for improving coloring and dispersion property of pigment in the field of dye and pigment industry, or an agent for improving leveling and anti-cratering property to thereby reduce coating defects.

Japanese Patent Application No. 2010-146251 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polyether-modified polysiloxane containing a perfluoropolyether group represented by the following general formula (1):

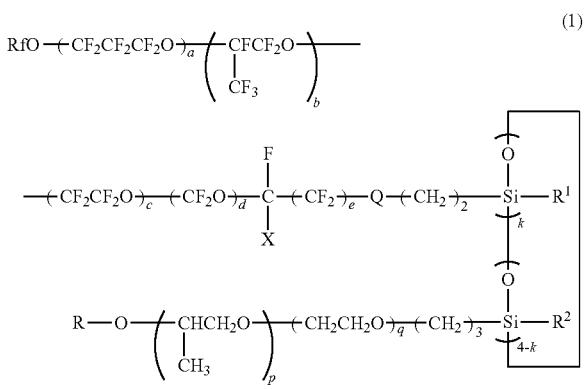

wherein Rf represents a straight chain or branched perfluoroalkyl group containing 1 to 10 carbon atoms; X represents fluorine atom or trifluoromethyl group; Q represents a divalent organic group containing 1 to 12 carbon atoms; R represents an alkyl group or acyl group containing 1 to 6 carbon atoms; $R^1$ and $R^2$ are independently an alkyl group, aryl group, or an aralkyl group containing 1 to 10 carbon atoms; a, b, c, d are independently an integer of 0 to 200 with the proviso that a+b+c+d is at least 1; e is 0 or 1; p and q are independently an integer of 0 to 50 with the proviso that p+q is at least 2; and k is an integer of 1 to 3.

2. A polyether-modified polysiloxane containing a perfluoropolyether group according to claim 1 represented by the following general formula (2):

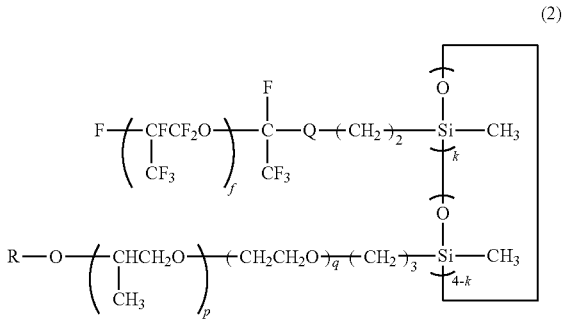

wherein Q, R, p, q, p+q, and k are as described above, and f is an integer of 2 to 200.

3. A polyether-modified polysiloxane containing a perfluoropolyether group according to claim 1 wherein content of the fluorine atom by weight in the molecule is in the range of 20 to 70% by weight.

4. A method for producing a polyether-modified polysiloxane containing a perfluoropolyether group according to claim 1 comprising: steps of
reacting a vinyl group-containing perfluoropolyether represented by the following general formula (3):

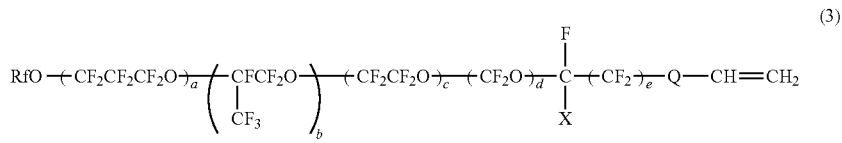

(3)

wherein Rf, X, Q, a, b, c, d, a+b+c+d, and e are as described above with a tetraorganocyclotetrasiloxane for hydrosilylation to produce a perfluoropolyether-modified cyclotetrasiloxane; and reacting the perfluoropolyether-modified cyclotetrasiloxane with an allyl group-containing polyether compound represented by the following general formula (4):

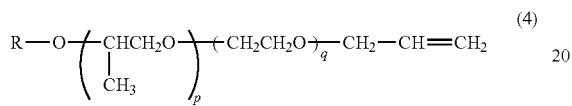

(4)

wherein R, p, q, and p+q are as described above for hydrosilylation to produce the polyether-modified polysiloxane containing a perfluoropolyether group.

* * * * *